(12) United States Patent
Saigusa et al.

(10) Patent No.: US 7,261,414 B2
(45) Date of Patent: Aug. 28, 2007

(54) OPHTHALMOLOGIC APPARATUS

(75) Inventors: Akio Saigusa, Tochigi (JP); Takeshi Kitamura, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 944 days.

(21) Appl. No.: 10/616,329

(22) Filed: Jul. 8, 2003

(65) Prior Publication Data

US 2004/0008321 A1    Jan. 15, 2004

(30) Foreign Application Priority Data

Jul. 10, 2002 (JP) ............................ 2002-201600

(51) Int. Cl.
*A61B 3/14* (2006.01)
(52) U.S. Cl. ................. 351/208; 351/205; 351/206
(58) Field of Classification Search ................. 351/208
See application file for complete search history.

(56) References Cited

U.S. PATENT DOCUMENTS

| | | | | |
|---|---|---|---|---|
| 4,733,229 A * | 3/1988 | Whitehead | ............... | 345/20 |
| 4,985,848 A * | 1/1991 | Pfeiffer et al. | ............. | 345/505 |
| 6,584,235 B1 * | 6/2003 | Fossum et al. | ............ | 382/284 |
| 6,736,507 B2 * | 5/2004 | Kudryashov et al. | ....... | 351/206 |
| 2001/0028438 A1 | 10/2001 | Matsumoto | | |
| 2001/0028439 A1 * | 10/2001 | Itoh | ........................ | 351/206 |
| 2002/0156019 A1 * | 10/2002 | Foster | ....................... | 514/21 |

FOREIGN PATENT DOCUMENTS

| | | |
|---|---|---|
| CN | 1154907 | 6/2004 |
| JP | 4-38582 | 2/1992 |
| JP | 5-199998 | 8/1993 |
| JP | 7-262081 | 10/1995 |
| KR | 1999-0075162 | 10/1999 |

OTHER PUBLICATIONS

Korean Official Letter/Search Report dated Sep. 29, 2005.
Japanese translation of Korean Official Letter/Search Report dated Sep. 29, 2005.
Chinese Search Report and Office Action dated Jun. 17, 2005 with English translation of Official Action of Chinese Patent Office.

* cited by examiner

*Primary Examiner*—Scott J. Sugarman
*Assistant Examiner*—DaWayne A Pinkney
(74) *Attorney, Agent, or Firm*—Morgan & Finnegan, LLP

(57) ABSTRACT

There is provided an ophthalmologic apparatus capable of changing a gain to a digitized image signal according to observation and image taking operations by rewriting data in an LUT or selecting a suitable LUT from a plurality of LUTs.

3 Claims, 3 Drawing Sheets

OPHTHALMOLOGIC APPARATUS

BACKGROUND OF THE INVENTION

1. Field of the Invention

The present invention relates to an ophthalmologic apparatus used in an ophthalmologic clinic and the like.

2. Related Background Art

In recent years, a large number of apparatuses using image pickup elements have been developed. Even in ophthalmologic image taking apparatuses, ophthalmologic apparatuses in which an image of an eye to be examined is obtained as an electronic image using image pickup elements instead of a conventional silver-halide film have been developed to conduct electronic filing, a remote diagnosis, a diagnostic support using a computer, and the like.

According to such an ophthalmologic apparatus, for example, in the case of a non-mydriatic eye fundus camera, focusing and alignment adjustment are conducted using infrared light by a monochrome camera at the time of observation. In addition, a still image is picked up in synchronization with strobe light using another color camera at the time of image taking.

However, in recent years, an eye fundus camera comes to be used which includes not respective special image pickup elements for infrared observation and color still image taking which are used in a conventional apparatus but a common image pickup element.

When the common image pickup element is used for observation and image taking, a light source for observation using infrared light is different from a light source for color still image taking using strobe light. Therefore, in order to obtain suitable images at the observation and the image taking, it is necessary to set respective different gains.

For example, as disclosed in Japanese Patent Application Laid-Open No. 04-038582, there has been a method in which a gain of a camera is increased at the time of observation with low illumination to improve a contrast in an image and a gain of a camera is reduced at the time of image taking with high illumination to improve an S/N ratio of a taken image.

Thus, according to the above-mentioned conventional example, the gain of the observation camera and the amount of light from the observation light source are adjusted to improve the contrast in the observation image. However, when the gain and the amount of light are simply changed, a contrast in the entire image including an aperture region is enhanced. Therefore, it is impossible to enhance a contrast in only a region of interest such as a blood vessel which becomes an index in focusing and alignment adjustment. Accordingly, a sufficient contrast cannot be obtained by only adjusting the gain and the amount of light, so that there is the case where it is difficult to conduct focusing and alignment adjustment.

FIG. 4 is a histogram of the entire image in observation. The abscissa indicates brightness and the ordinate indicates a frequency. In FIG. 4, brightness levels of an aperture region are distributed in a range "A", brightness levels of the entire eye fundus are distributed in a range "B", and brightness levels of blood vessels near an optic disk portion which are used for focusing and alignment adjustment are distributed in a range "C".

When infrared light is used as observation light, the reflection from not a retina but a choroid becomes dominant, so that a range in which image data of the region of interest on the retina are distributed is extremely narrow as shown in FIG. 4. Therefore, the contrast in the region of interest cannot be almost improved by only a linear correction such as the adjustment for the gain of the camera and the amount of observation light.

On the other hand, in the case of still image taking using strobe light, a correction method is desired which is different from a correction at the time of observation such as a gamma correction for monitor or a linear gain correction. Therefore, in order to improve the contrast in the observation image, a special correction circuit for observation is required as disclosed in Japanese Patent Application Laid-Open No. 05-199998. When such a special correction circuit is used, the entire circuit is upsized and complicated, thereby increasing a cost.

SUMMARY OF THE INVENTION

An object of the present invention is to solve the above-mentioned problems and to provide an ophthalmologic apparatus capable of improving a contract in a region of interest such as a blood vessel at observation without using a special correction circuit for observation.

In order to achieve the above-mentioned object, according to one aspect of the present invention, an ophthalmologic apparatus includes: observation illumination means for illuminating an eye fundus of an eye to be examined in observation operation; image taking illumination means for illuminating the eye fundus in image taking operation; image pickup means for electrically converting an image of the eye fundus obtained by both the illumination means into an image signal; conversion means for converting the image signal obtained by the image pickup means into a digital value; a frame memory for storing the digital value data of the image signal; a rewritable lookup table; and rewrite means for rewriting the data in the lookup table in synchronization with the observation operation and the image taking operation.

Further, according to another aspect of the present invention, an ophthalmologic apparatus includes: observation illumination means for illuminating an eye fundus of an eye to be examined in observation operation; image taking illumination means for illuminating the eye fundus in image taking operation; image pickup means for electrically converting an image of the eye fundus obtained by both the illumination means into an image signal; conversion means for converting the image signal obtained by the image pickup means into a digital value; a plurality of lookup tables for storing different data for correcting the digital value of the image signal; and selection means for selecting a desired lookup table from the plurality of lookup tables in accordance with the observation operation and the image taking operation.

DESCRIPTION OF THE PREFERRED EMBODIMENTS

Figure 1:
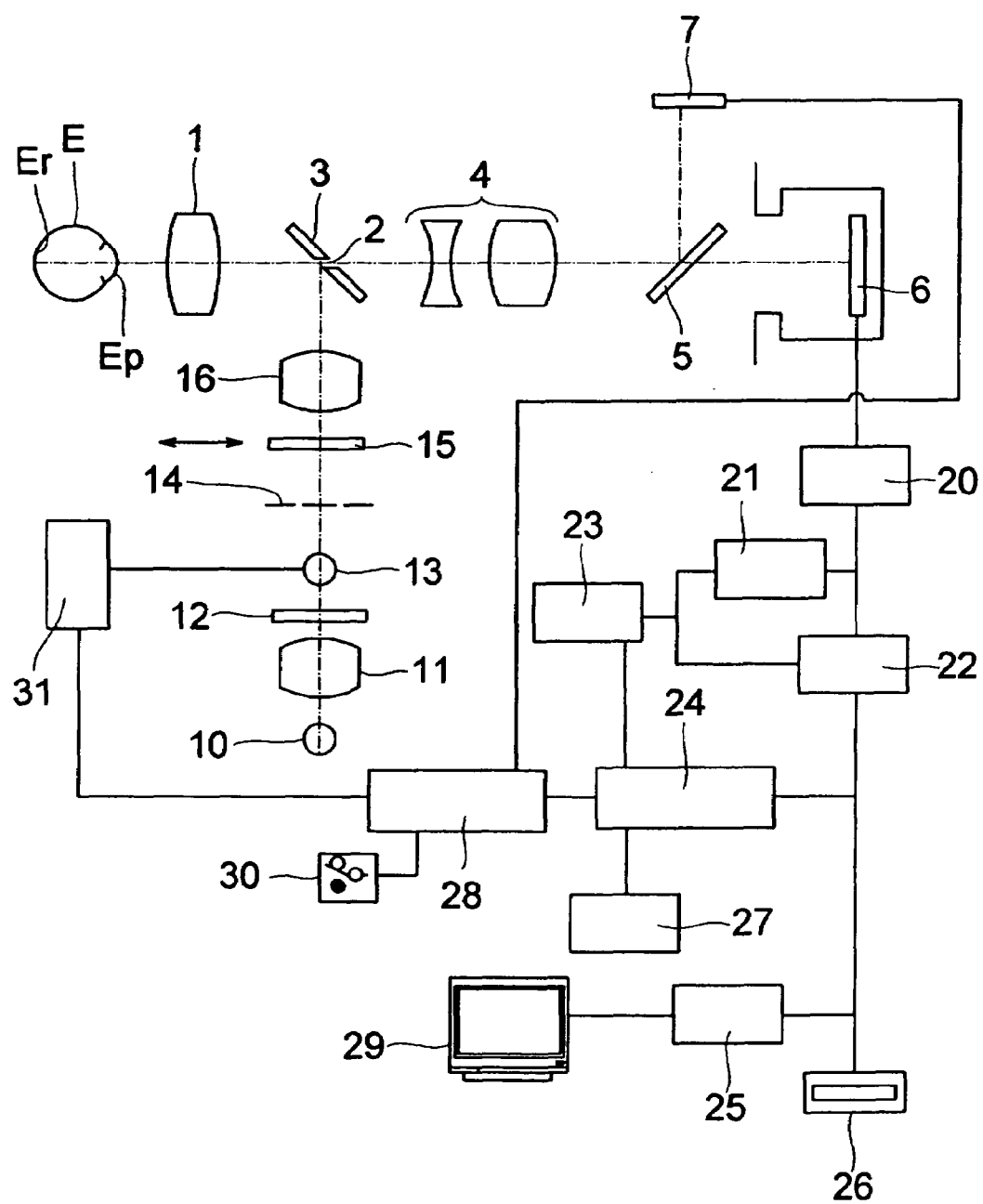
FIG. 1 is a structural diagram of an eye fundus camera.

The present invention will be described in detail based on an embodiment shown in the drawings.

FIG. 1 is a structural diagram of an eye fundus camera according to a first embodiment of the present invention.

In front of an eye to be examined E, an objective lens 1 is disposed as an eye fundus observation and image taking optical system. On an optical path in the rear of the objective lens 1, a holed mirror 3 having an image taking diaphragm 2 in a hole portion, an image taking lens 4 a part of which is moveable along the optical path for focusing, a half mirror 5, and an image pickup unit 6 such as a television camera are arranged in order.

In the light reflecting direction of the half mirror 5, a fixation light 7 conjugate with an eye fundus Er is disposed to present a fixation target to the eye to be examined E. The fixation light 7 is composed of, for example, an LED array in which LEDs are arranged in dot matrix, or a backlight made from LEDs or the like and a dot matrix liquid crystal shutter. Therefore, light transmission/non-transmission of a dot at an arbitrary position of a two-dimensional matrix is controlled, so that the fixation target can be presented at the arbitrary position for the eye to be examined E. Note that an external fixation light is separated from the image taking optical system and used as the fixation light.

Also, in an illumination optical system located on a light incident side of the holed mirror 3, an observation light source 10 such as a halogen lamp for emitting visible light, a condenser lens 11, a visible cutting filter 12 for cutting off the visible light, a strobe light source 13 for emitting a flash of visible light, a diaphragm 14 having a ring-shaped opening, an infrared cutting filter 15 for cutting off infrared light, and a lens 16 are arranged in order from the observation light source 10 side.

An output of the image pickup unit 6 is connected with a frame memory 21 and an LUT (lookup table) 22 through an A/D converting section 20. The frame memory 21 is connected with an LUT setting section 23 and the LUT 22. An output of the LUT 22 and an output of the LUT setting section 23 are connected with an image control section 24.

The image control section 24 is connected with a D/A converting section 25, a recording medium 26, an information input unit 27, and a control circuit 28. An output of the D/A converting section 25 is connected with a monitor 29. The control circuit 28 is connected with a right-and-left-eye selection switch 30 and connected with the strobe light source 13 through a strobe light emission control circuit 31.

First, before image taking, a file format used in the case where patient information such as an ID number, a name, a birth date, and a sex of a person to be examined and a taken image are outputted is inputted to the image control section 24 through the information input unit 27 by a photographer. Subsequently, the objective lens 1 is located in the front of the eye to be examined E and the observation light source 10 for eye fundus observation is turned on. Light from the observation light source 10 is condensed by the condenser lens 11. Visible light of the condensed light is cut off by the visible cutting filter 12. Observation light considered to be infrared light passes through the strobe light source 13, the diaphragm 14, and the lens 16, is reflected to the left by a mirror portion of the holed mirror 3, and passes through the objective lens 1 to illuminate the eye fundus Er through a pupil Ep of the eye to be examined E.

At this time, the infrared cutting filter 15 is removed from the optical path by a mechanism which is not shown. Then, an image of the eye fundus illuminated with the observation light is again passed through the objective lens 1, the image taking diaphragm 2 of the holed mirror 3, and the image taking lens 4, transmitted through the half mirror 5, and formed onto the image pickup unit 6.

The image pickup unit 6 which is sensitive to infrared light and visible light converts the received eye fundus image into a video signal and then outputs the obtained video signal to the A/D converting section 20. The video signal which is inputted to the A/D converting section 20 is converted from analog data to digital data. Observation image data corresponding to a frame of the image of the eye to be examined, which is converted into the digital data, is stored in the frame memory 21.

Figure 2:
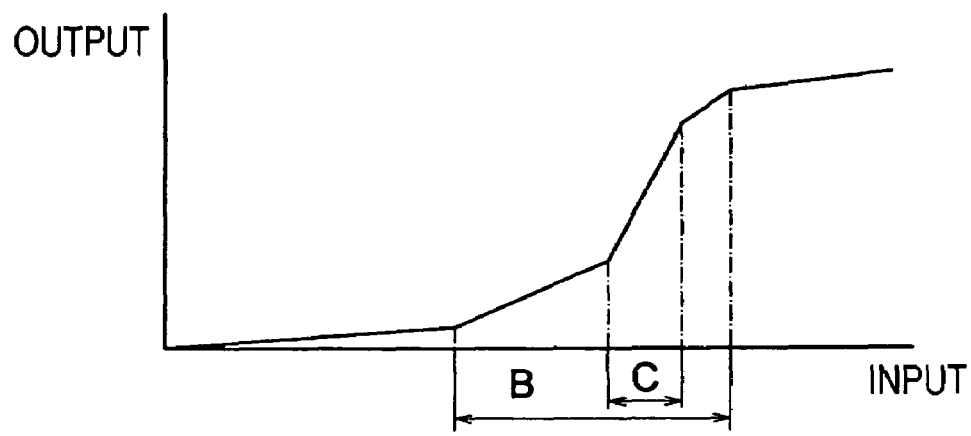
FIG. 2 is a graph of a lookup table (LUT) at the time of observation.
Figure 4:
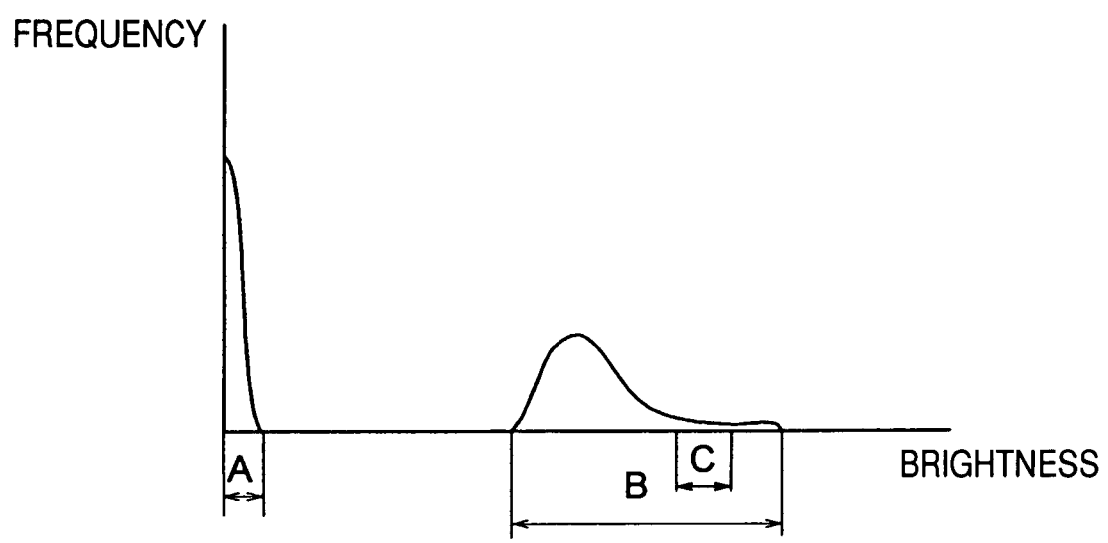
FIG. 4 is a histogram of image data in infrared observation.

Next, the LUT setting section 23 extracts a histogram from image data stored in the frame memory 21, produces an observation LUT for enhancing an image region such as a blood vessel on a retina with respect to ranges B and C as shown in FIG. 4, for example, the LUT as shown in FIG. 2, and sets the observation LUT in the LUT 22.

Also, image data outputted from the A/D converting section 20 is inputted to the LUT 22, subjected to gradation conversion by the LUT 22 which is set as described above, and then outputted to the D/A converting section 25. The D/A converting section 25 converts inputted digital data into an analog signal and then outputs the analog signal to the monitor 29.

Thus, an observation image such as a blood vessel image in which a contrast in a region of interest is enhanced is displayed on the monitor 29. While observing an eye fundus image displayed on the monitor 29, the photographer conducts precision alignment between the eye to be examined E and the image pickup unit, focusing, and checking of an image taking area. After it is ensured that the image taking area, the alignment, and the focusing are preferable, the photographer operates an image taking switch which is not shown to conduct still image taking.

The control circuit 28 which has detected the input by the image taking switch is adapted to insert the infrared cutting filter 15 onto the optical path and output an image taking start signal to the image control section 24. After that, the control circuit 28 waits a light emission timing signal for the strobe light source 13 which is outputted from the image control section 24.

When the light emission timing signal for the strobe light source 13 is received by the control circuit 28, the control circuit 28 sends a light emission signal to the strobe light emission control circuit 31 without delay, thereby emitting a light flux from the strobe light source 13. The light flux emitted from the strobe light source 13 passes through the objective lens 1 to illuminate the eye fundus Er of the eye to be examined E as in the case of the observation light. The eye fundus image is formed onto the image pickup surface of the image pickup unit 6, so that a video signal is outputted to the A/D converting section 20.

Figure 3:
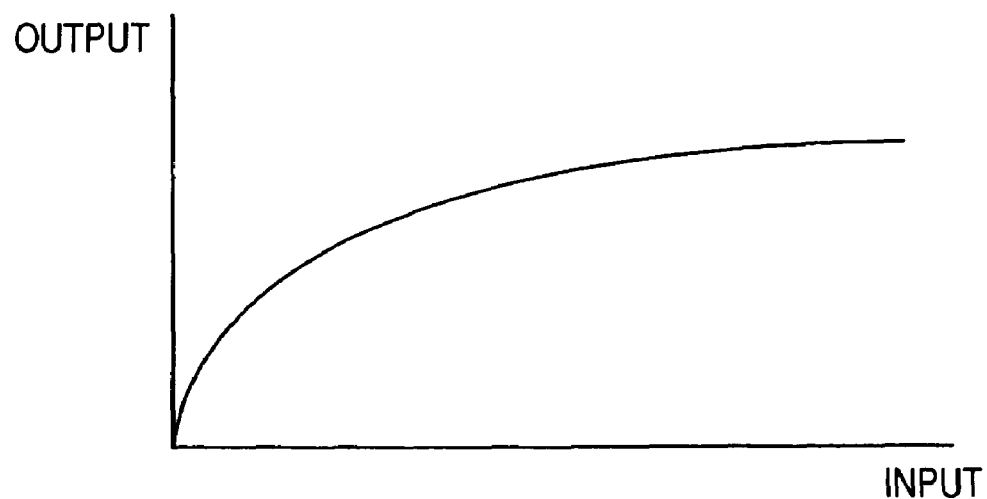
FIG. 3 is a graph of an LUT at the time of image taking operation.

The image control section 24 synchronizes a video signal corresponding to a frame which is outputted from the image pickup unit 6 with strobe light emission. The video signal is converted into digital data by the A/D converting section 20 and then stored in the frame memory 21. Next, an LUT for still image taking, for example, an LUT for correcting a gamma characteristic of the monitor 29 as shown in FIG. 3 is produced in the LUT setting section 23 and is set in the LUT 22.

Subsequently, eye fundus image data stored in the frame memory 21 is read out and subjected to gradation conversion by the LUT 22. After that, the eye fundus image data is converted into an image format such as BMP or a set compression ratio to convert the data into an image format such as JPEG, and the data is recorded on the recording medium 26 such as a MO or a hard disk.

If necessary, the image control section 24 reads out the image data from the frame memory 21. The image data is subjected to gradation conversion by the LUT 22, and then inputted to the D/A converting section 25 and outputted to the monitor 29. Therefore, the photographer can check the image.

When the A/D converting section 20, the frame memory 21, and the LUT 22 are provided as in this embodiment, it becomes possible to set an LUT for image correction after image taking. Accordingly, a period from image taking to image acquisition can be shortened.

Note that, in this embodiment, when the LUT at the time of observation is produced, the region of interest is linearly enhanced using histogram data of the observation image. However, the present invention is not limited to such an example. Histogram smoothing or the like can be conducted without using histogram data of an aperture region. In addition, when a level of the region of interest at the time of observation is predictable from the gain of a camera, the amount of observation light, or the like, a previously fixed LUT may be used.

Also, the LUT for correcting the gamma characteristic of the monitor 29 is used as the LUT for still image taking. However, the present invention is not limited to this. A linear LUT, an LUT for enhancing a macular portion and an optic disk portion, or the like may be used. Further, when a characteristic of a light source is changed, another LUT or the like may be used according to the characteristic of the light source. In addition, data written into an LUT can be changed. Alternatively, the LUT 22 may have a plurality of LUTs. Data for observation is written into an LUT and data for image taking which is different from the data for observation is written into another LUT.

Note that, in the conventional example, the data obtained by A/D conversion is stored in the frame memory and then subjected to gradation conversion by the LUT. However, the data obtained by A/D conversion may be subjected to gradation conversion by the LUT and then stored in the frame memory.

A recording medium in which a program is stored according to this embodiment can be supplied to another system or apparatus. In this case, a computer in the system or apparatus can read out program codes stored in the recording medium and execute the above-mentioned steps.

As described above, according to the ophthalmologic apparatus in the present invention, optimum images can be easily obtained in observation and image taking without using the special correction circuit for observation.

What is claimed is:

1. An ophthalmologic apparatus comprising:
observation illumination means for illuminating an eye fundus of an eye to be examined with infrared light in moving image observation operation;
image taking illumination means for illuminating the eye fundus in static image taking operation;
image pickup means for converting an image of the eye fundus of the eye to be examined into an image signal;
conversion means for converting the image signal into a digital data;
a plurality of lookup tables;
setting means for setting a first lookup table of the plurality of the lookup tables in the moving image observation operation, and setting a second lookup table of the plurality of the lookup tables in the static image taking operation; and
gradation conversion means for gradationally converting the digital data by using the lookup table set by the setting means,
wherein the first lookup table is used so as to enhance a region of a blood vessel on a retina image formed on the basis of a histogram calculated from the digital data.

2. An ophthalmologic apparatus according to claim 1, further comprising a monitor for displaying a digital data after gradationally converted.

3. An ophthalmologic apparatus comprising:
observation illumination means for illuminating an eye fundus of an eye to be examined with infrared light in moving image observation operation;
image taking illumination means for illuminating the eye fundus in static image taking operation;
image pickup means for converting an image of the eye fundus of the eye to be examined into an image signal;
conversion means for converting the image signal into a digital data;
a plurality of lookup tables;
setting means for setting a first lookup table of the plurality of the lookup tables in the moving image observation operation, and setting a second lookup table of the plurality of the lookup tables in the static image taking operation; and
gradation conversion means for gradationally converting the digital data by using the lookup table set by the setting means,
wherein the first lookup table is formulated on the basis of a gain of the image pickup means and amount of light from the observation illumination means.

* * * * *